(12) United States Patent
Ito

(10) Patent No.: US 6,702,249 B2
(45) Date of Patent: *Mar. 9, 2004

(54) PRESSURE-VARIABLE VALVE DEVICE AND SET-PRESSURE ADJUSTING DEVICE FOR THE VALVE DEVICE

(75) Inventor: Takashi Ito, Chiba (JP)

(73) Assignee: Seiko Instruments Inc., Chiba (JP)

( * ) Notice: Subject to any disclaimer, the term of this patent is extended or adjusted under 35 U.S.C. 154(b) by 21 days.

This patent is subject to a terminal disclaimer.

(21) Appl. No.: 10/287,070

(22) Filed: Nov. 4, 2002

(65) Prior Publication Data

US 2003/0057392 A1 Mar. 27, 2003

Related U.S. Application Data

(62) Division of application No. 09/811,989, filed on Mar. 19, 2001, now Pat. No. 6,485,449.

(51) Int. Cl.$^7$ .............................. A61B 5/03; A61M 1/00
(52) U.S. Cl. ...................... 251/65; 251/230; 137/530; 604/9
(58) Field of Search ..................... 251/65, 230; 604/9, 604/891.1; 137/530, 531

(56) References Cited

U.S. PATENT DOCUMENTS

| | | | | |
|---|---|---|---|---|
| 4,360,007 A | * | 11/1982 | Levy et al. | 251/230 X |
| 4,540,400 A | * | 9/1985 | Hooven | 251/65 X |
| 4,595,390 A | * | 6/1986 | Hakim et al. | 137/530 X |
| 4,615,691 A | * | 10/1986 | Hakim et al. | 604/9 |
| 4,772,257 A | * | 9/1988 | Hakim et al. | 604/9 |
| 5,643,194 A | * | 7/1997 | Negre | 251/65 X |
| 5,928,182 A | * | 7/1999 | Kraus et al. | 604/9 |
| 6,050,969 A | * | 4/2000 | Kraus | 604/9 |
| 2001/0022350 A1 | | 9/2001 | Ito | 251/65 |

FOREIGN PATENT DOCUMENTS

EP 0888795 1/1999

* cited by examiner

*Primary Examiner*—Michael Mar
*Assistant Examiner*—Eric Keasel
(74) *Attorney, Agent, or Firm*—Adams & Wilks (57) ABSTRACT

A pressure-variable valve device which is adapted to be embedded in the human body and which is capable of changing a difference in pressure between an inlet-side and an outlet-side duct, the valve device including a rotating member capable of rotating around a central axis in directions to vary a set pressure for a valve, and a rotation control mechanism for controlling the rotation of the rotating member, wherein the rotation control mechanism includes permanent magnet structures supported by the valve-device main body so as to be capable of making a linear reciprocal translation in directions, and displacement transmission mechanisms, for rotating the rotating member in the direction corresponding to the direction of the translation of the permanent magnet structures. A set-pressure adjusting device includes a magnetic field generating mechanism which generates a magnetic field in which the permanent magnet structures cause the rotating member to rotate in the same direction.

20 Claims, 7 Drawing Sheets

PRESSURE-VARIABLE VALVE DEVICE AND SET-PRESSURE ADJUSTING DEVICE FOR THE VALVE DEVICE

This is a continuation of Ser. No. 09/811,989, filed Mar. 19, 2001 now U.S. Pat. No. 6,485,449.

BACKGROUND OF THE INVENTION

1. Field of the Invention

The present invention relates to a pressure-variable valve device and, more specifically, to a pressure-variable valve device suitable for use as a shunt valve embedded in the human body to adjust the pressure of the spinal fluid or the like, and to a set-pressure adjusting device therefor.

2. Description of the Prior Art

Japanese Patent Application Laid-Open No. 60-40063 discloses a technique for treatment for hydrocephalus or the like in which the pressure of the spinal fluid or the like is adjusted by providing in the flow passage of the spinal fluid or the like a shunt valve (branch valve) device in which the forward ends of arm portions on both sides of a fork-like plate spring are locked, and the forward end of a central arm portion is held in contact with a ball serving as a valve, and in which the base end portion of the fork is engaged with a spiral cam surface formed on a rotating member rotatable around a central axis, and the engagement base portion of the spring is moved in the axial direction of the rotating member in accordance with the rotation of the cam surface as a result of the rotation of the rotating member to vary the deflection amount of the spring, thereby varying the pressure applied to the ball by the spring. In this shunt valve device, a ratchet having claws on the peripheral surface is formed integrally with the rotating member, and two engagement members are arranged opposite to the claws of the ratchet, each engagement member being rotatable around a fulcrum situated in the intermediate portion with respect to the longitudinal direction and having at both ends engagement pawls which can be engaged with the claws of the ratchet. Further, magnets are mounted to the engagement members such that the adjacent end portions of the two engagement members are of the same polarity. When a magnetic field is applied in one direction from outside, the two engagement members rotate in the same direction around their respective rotation axes to cause the ratchet to rotate in a direction corresponding to the direction of the above rotation. Next, a reverse magnetic field is applied to restore the two engagement members to the original rotating positions. By repeating these operations, the rotating position of the rotating member is adjusted (FIGS. 10a through 10d and FIG. 11 of the above-mentioned publication).

However, in this set-pressure-variable shunt valve or pressure-variable valve device, there is the danger that an undesired change in the set pressure occurs in an environment in which the direction of the external magnetic field applied to the entire shunt valve varies. That is, when a patient suffering from hydrocephalus or the like, under whose scalp the shunt valve is embedded, undergoes inspection and diagnosis of the head by an MRI (magnetic resonance imaging) apparatus, the patient, in a typical case, moves the head portion to be inspected and diagnosed in various directions in the MRI apparatus with respect to the strong and spatially uniform main magnetic field applied in the Z-direction of the apparatus, with the result that there is applied to the shunt valve portion a magnetic field whose direction varies in the same sequence as when the rotating position of the rotating member of the shunt valve is adjusted, thereby causing an undesired deviation in the set pressure.

SUMMARY OF THE INVENTION

The present invention has been made in view of the above problem in the prior art. It is accordingly an object of the present invention to provide a pressure-variable valve device in which there is little danger of the set pressure being deviated even in the main magnetic field of an MRI apparatus, and a set-pressure adjusting device for such a valve device.

To achieve the above object, there is provided, in accordance with the present invention, a pressure-variable valve device which is adapted to be embedded in the human body and which is capable of changing a difference in pressure between an inlet-side duct and an outlet-side duct, the valve device comprising a rotating member capable of rotating around a central axis inside a valve-device main body to vary a set pressure of a valve, and a rotation control mechanism for controlling the rotation of the rotating member, wherein the rotation control mechanism includes at least one permanent magnet structure supported by the valve-device main body so as to be capable of making a linear reciprocal translation in the valve-device main body, and a displacement transmission mechanism for rotating the rotating member in a direction corresponding to the direction of the translation of the permanent magnet structure.

In the pressure-variable valve device of the present invention, there are provided "at least one permanent magnet structure supported by the valve-device main body so as to be capable of making a linear reciprocal translation in the valve-device main body, and a displacement transmission mechanism for rotating the rotating member in a direction corresponding to the direction of the translation of the permanent magnet structure", so that, by applying to a portion in the vicinity of the permanent magnet structure a magnetic field which causes the permanent magnet structure to make a translation movement in a direction corresponding to the direction of rotation of the rotating member by the displacement transmission mechanism (When there are a plurality of permanent magnet structures, the direction of translation of each permanent magnet structure is made the same as the direction of the torque applied to the rotating member), it is possible to rotate the rotating member in a desired direction. Further, in the pressure-variable valve device of the present invention, the rotating member is "capable of rotating around a central axis inside a valve-device main body to vary a set pressure of a valve", so that, by rotating the rotating member, it is possible to change the set pressure of the valve device, that is, the difference in pressure between the inlet-side duct and the outlet-side duct.

Further, in the pressure-variable valve device of the present invention, the permanent magnet structure is "supported by the valve-device main body so as to be capable of making a linear reciprocal translation in the valve-device main body", so that, when the pair of magnetic poles (N, S) of the permanent magnet structure are simultaneously exposed to a magnetic field of the same direction and of actually the same strength like the main magnetic field in the Z-direction of an MRI apparatus, the forces causing the permanent magnet structure to make a translation are balanced, the forces applied to the magnetic poles being of the same magnitude and opposite directions. Thus, the permanent magnet structure is not actually caused to make a translation movement, and no torque is imparted to the rotating member, so that there is no danger of the rotating member being caused to rotate. That is, even when a person in whose body a pressure-variable valve device of the present invention is embedded is placed in the strong main magnetic field of an MRI apparatus for inspection or diagnosis, there is little danger of the rotating member of the valve device making an unexpected rotation and little danger of the set pressure of the valve device being changed.

In the valve device of the present invention, as long as it is possible to change the difference in pressure between the inlet-side duct and the outlet-side duct, the valve of the valve device may be of the type which normally keeps the flow passage closed and allows the inlet-side duct to communicate with the outlet-side duct when the set pressure is reached (normally-closed type), or of the type which normally keeps the valve flow passage open and in which the size of the aperture of the valve flow passage determines the difference in pressure between the inlet-side duct and the outlet-side duct (normally-open type). In the case of the former type, the set pressure is changed or adjusted by changing or adjusting the pressure at which the closure of the valve flow passage by the valve is canceled, and in the case of the latter type, the flow rate varies by changing or adjusting the aperture size of the valve flow passage throttled by the valve, thereby changing or adjusting the set pressure. Here, the terms: "inlet-side duct" and "outlet-side duct" mean ducts, conduits or flow passages at the inlet and outlet of the valve device.

There is no particular restriction regarding the way the rotating member is supported as long as it is capable of rotating around the central axis. The term "central axis" means the central axis of rotation or the rotation axis. The configuration of the rotating member is typically substantially symmetrical with respect to the central axis. Strictly speaking, however, it may also be asymmetrical. Further, the central axis, that is, the rotation axis may be offset from the central portion of the rotating member. At the time of rotation, the rotation member may move or not move along the rotation axis.

The permanent magnet structure typically consists of a permanent magnet having magnetic poles of opposite polarities at both ends. However, it is only necessary for the structure to behave as one permanent magnet as a whole with respect to an external magnetic field, and there is no particular restriction regarding the construction for magnetizing the interior of each structure. For example, the entire structure may consist of a permanent magnet, or one or more permanent magnets may be fixed or embedded at one or a plurality of positions. Further, in some cases, the magnetic pole may be situated at a side surface in the vicinity of an end portion so that the influence of the magnetic field formed by the set-pressure adjusting device arranged on the body surface may be easily had.

Preferably, the rotation control mechanism has a pair of magnet structures, and the displacement transmission mechanism is constructed such that, when substantially the same external magnetic field is applied to the pair of magnet structures, mutually balancing, reversely directed torques are imparted to the rotating member.

In this case, due to the influence, for example, of an inclined magnetic field, etc. applied in the MRI apparatus in order to provide a resonance frequency which differs from place to place, the magnitudes of the magnetic fields applied to the N-pole and the S-pole of the permanent magnet structure are different, so that, even when a force in the translating direction which is of some magnitude as a whole is applied to the permanent magnet structures, the pair of magnet structures impart mutually balancing torques to the rotating member. Thus, there is little danger of the rotating member being caused to rotate unexpectedly.

Preferably, the rotation control mechanism includes a pair of permanent magnet structures which are substantially opposed to each other in a diametral direction with respect to the central axis of the rotating member and which are capable of making a translation movement substantially in parallel in a direction crossing the diametral direction, the structures respectively having magnetic poles of the same polarity at an end on the same side with respect to the direction in which translation movement is possible, and a displacement transmission mechanism which causes an adjacent portion of the rotating member to move in a direction (the same direction) corresponding to the direction of the translation movement of one of the pair of permanent magnet structures, and which causes the adjacent portion of the rotating member to move in a direction (the same direction) corresponding to the direction of the translation movement of the other permanent magnet structure.

In this case, there are provided "a pair of permanent magnet structures which are substantially opposed to each other in a diametral direction with respect to the central axis of the rotating member and which are capable of making a translation movement substantially in parallel in a direction crossing the diametral direction, the structures respectively having magnetic poles of the same polarity at an end on the same side with respect to the direction in which translation movement is possible". Thus, when exposed to a magnetic field which is uneven or which is not uniform like the inclined magnetic field of an MRI apparatus, the pair of permanent magnet structures having magnetic poles of the same polarity at an end portion on the same side receive a force which causes them to make a translation movement in the same direction as long as the magnetic field is an abnormal magnetic field having a singular point. Further, there is provided "a displacement transmission mechanism which causes an adjacent portion of the rotating member to move in a direction (the same direction) corresponding to the direction of the translation movement of one of the pair of permanent magnet structures, and which causes the adjacent portion of the rotating member to move in a direction (the same direction) corresponding to the direction of the translation movement of the other permanent magnet structure". Thus, when one of the pair of permanent magnet structures is caused to make a translation movement in one direction, an adjacent portion of the rotating member moves in the above direction to receive a force causing rotation in one direction, and the other permanent magnet structure which is substantially diametrally opposed thereto with respect to the central axis of the rotating member is also caused to make a translation movement in the same direction, that is, the above-mentioned direction, to cause the adjacent portion of the rotating member to move in the above direction and generate a force which causes the rotating member to rotate in the other direction. As a result, the rotation of the rotating member is mutually restrained or inhibited. Thus, even when inspection or diagnosis is conducted by an MRI apparatus or the like, it is possible to minimize the danger of the rotating member being caused to rotate unexpectedly. As a result, there is little danger of the set pressure of the valve device being unexpectedly changed by the rotation of the rotating member.

On the other hand, by forming a magnetic field which causes one of the pair of magnet structures to move in one direction and causes the other magnet structure to move in the other direction in the vicinity of at least one magnetic pole of each permanent magnet structure, an additive torque which causes portions of the rotating member diametrally opposed to each other to move in opposite directions is imparted to the rotating member, with the result that the rotating member receives torques in the same direction from the pair of permanent magnet structures, and is rotated in that direction, thereby making it possible to change the set pressure of the valve device in correspondence with the rotation.

For the pair of permanent magnet structures to impart mutually balancing opposite torques to the rotating member in a magnetic field inclined in one direction, it is possible to adopt, instead of the construction in which there are provided "a pair of permanent magnet structures which are substantially opposed to each other in a diametral direction with respect to the central axis of the rotating member and which are capable of making a translation movement substantially in parallel in a direction crossing the diametral direction, the structures respectively having magnetic poles of the same polarity at an end on the same side with respect to the direction in which translation movement is possible", a construction in which "the structures respectively have magnetic poles of opposite polarities at an end portion on the same side in the direction in which a translation movement is possible", and, regarding the displacement transmission mechanism, it is possible to adopt in stead of the construction "which causes an adjacent portion of the rotating member to move in a direction (the same direction) corresponding to the direction of the translation movement of one of the pair of permanent magnet structures, and which causes the adjacent portion of the rotating member to move in a direction (the same direction) corresponding to the direction of the translation movement of the other permanent magnet structure", it is possible to adopt a construction which causes an adjacent portion of the rotating member in one or the other direction upon the translation movement of one of the pair of permanent magnet structures in one or the other direction, and which "causes the adjacent portion of the rotating member in one or the other direction upon the translation movement of the other permanent magnet structure in one or the other direction". In the latter case, between the other magnet structure and the rotating member, there is further provided a displacement transmission mechanism, by means of which the displacement direction is reversed.

In these cases, the end portion at which the permanent magnet structure has a magnetic pole is typically an end edge of the structure. However, in some cases, it may also be some other portion such as a side surface in the vicinity of the end portion.

The displacement transmission mechanism may be constructed so as to convert the continuous transmission movement of the permanent magnet structure to a continuous rotation of the rotating member as it is. Typically, however, there is provided a one-direction clutch mechanism which makes an intermittent rotation by a unit pitch upon one translation movement of the permanent magnet structure in one direction.

In the valve device of the present invention, the displacement transmission mechanism preferably has a ratchet which coaxial with the rotating member and is formed integrally with the rotating member, and an engagement pawl connected to each permanent magnet structure so as to engage with an adjacent portion of a claw of the ratchet when each permanent magnet structure makes a translation movement. When making a translation movement in one direction or in the direction opposite thereto, the permanent magnet structure imparts a torque to the ratchet, so that there are provided a pair of engagement pawls for each permanent magnet structure.

In this case, each of the pair of engagement pawls connected to the permanent magnet structure may be in the form of a one-way clutch which imparts a torque to a claw of the ratchet in a translation movement in the corresponding direction and which imparts practically no torque to a claw of the ratchet in a translation movement in the returning direction. However, the rotation control mechanism preferably has a restraining spring or jumper spring provided with a restraining engagement end portion one end of which is engaged with the valve-device main body to cooperate with the engagement pawl of the permanent magnet structure to cause the rotating member to intermittently rotate in one-pitch unit of the claws of the ratchet and the other end of which is elastically pressed against the claw of the ratchet, wherein the restraining spring is constructed so as to restrain the rotation of the rotating member due to the pair of permanent magnet structures at the end of the restraining engagement end portion with a weak restraining force permitting the rotation of the rotating member. One end of the restraining spring may be fastened to the valve-device main body or simply locked thereto.

In this case, the restraining spring is constantly held in press contact with a claw of the ratchet at least to a slight degree, so that, even if the portion (e.g., the head) in which the valve-device is embedded is abruptly moved or if a slight mechanical impact is applied to the embedded portion, the ratchet is locked so as to prevent it from rotating freely to minimize the danger of unexpected rotation of the ratchet, thereby making it possible to minimize the danger of unexpected change in the set pressure of the valve device.

As long as it is integral with the rotating member, the ratchet may be integrally formed of resin or the like, or its components may be separately formed of metal or the like, fastening them together so as not to make relative rotation.

The permanent magnet structure typically has an elongated hole to be engaged with a guide pin formed in the valve-device main body so as to allow sliding in one direction. In this case, the displacement direction and the movable range of the permanent magnet structure can be reliably restricted due to the engagement between the guide pin and the elongated hole. However, as long as the permanent magnet structure can be supported so as to be capable of making a linear reciprocal translation movement in one direction without involving any play, and, typically, as long as it can be supported so as to be capable of making a linear reciprocal sliding movement, it is possible to adopt some other means to restrict the direction and range of the one-way displacement of the permanent magnet structure.

It is desirable that the components of the pressure-variable valve device be formed, as far as possible, of a material which is practically free from the fear of being seen in the image or disturbing the image when performing imaging by an MRI (magnetic resonance imaging) apparatus, that is a so-called MRI-free material. For example, it is desirable that a magnetic material be not used in the components other than the permanent magnet structure, which should constitute a permanent magnet. Further, when, for example, the MRI apparatus is of the type which utilizes proton NMR, it is desirable to use a material which is completely or relatively free from a resonance condition that is very close to the nuclear magnetic resonance condition of the hydrogen atoms to be observed in the portion to be inspected, such as the human head. Thus, it is desirable that the components of the pressure-variable valve device other than the permanent magnet structure (e.g., the valve-device main body and the rotating member) be formed of an MRI-free plastic material (e.g., silicon resin, polycarbonate or the like) or an MRI-free non-magnetic metal material. Since it is something to be embedded in the body, it goes without saying that an material harmful to the human body should be avoided.

To apply a predetermined magnetic field to a portion in the vicinity of one or a pair of permanent magnet structures in order to cause at least one of the permanent magnet structures of the pressure-variable valve device to make a translation movement to rotate the rotating member, a magnetic field generating means is arranged in close vicinity to each permanent magnet structure. Thus, the set-pressure adjusting device consists of such a magnetic field generating means. The magnetic field generating means typically consists of an electromagnet in which a soft magnetic substance of high magnetic permeability is inserted into a solenoid coil. The number of electromagnets may be one or two according to the number of magnet structures, or four or more according to the number of magnetic poles of the magnetic structures.

The valve device has a set-pressure signal generating means so that the set-pressure condition of the valve device can be detected from outside. The signal may be a magnetic signal like a static magnetic field (e.g., the strength or direction of a magnetic field or the way time-dependent fluctuations are effected), an electric signal like a static electric field (e.g., the strength or direction of an electric field or the way time-dependent fluctuations are effected), an electromagnetic signal like an electromagnetic field, or other kinds of signal. Since the rotating position of the rotating member varies according to the set pressure, it is possible to directly detect the rotating position or adopt an arrangement in which some other factor (e.g., the axial position) varies according to the rotation, detecting this other factor.

The valve device is designed to be embedded in the human body for a medical purpose or the like. Typically, it is designed to be surgically embedded in the human body in order to be used as a shunt valve for ventricle/abdominal-cavity shunt, ventricle/ventriculus-cordis shunt, etc. so that the pressure of the relevant fluid in the body can be non-invasively adjusted to treat hydrocephalus, brain tumor, arachnoid cyst or the like, and it can have a size of approximately several cm or less which is suitable for use when adjusting the pressure of spinal fluid or the like.

BRIEF DESCRIPTION OF THE DRAWINGS

A preferred form of the present invention is illustrated in the accompanying drawings in which:

FIG. 1 are diagrams showing the inner construction of the valve-device main body of a pressure-variable valve device according to a preferred embodiment of the present invention, in which

FIG. 7 are diagrams illustrating a set-pressure detecting device for detecting the set-pressure condition of the pressure-variable valve device shown in FIGS. 5 and 6, of which

DETAILED DESCRIPTION OF THE PREFERRED EMBODIMENTS

Next, a preferred embodiment of the present invention will be described with the accompanying drawings.

Embodiment

Figure 1A:
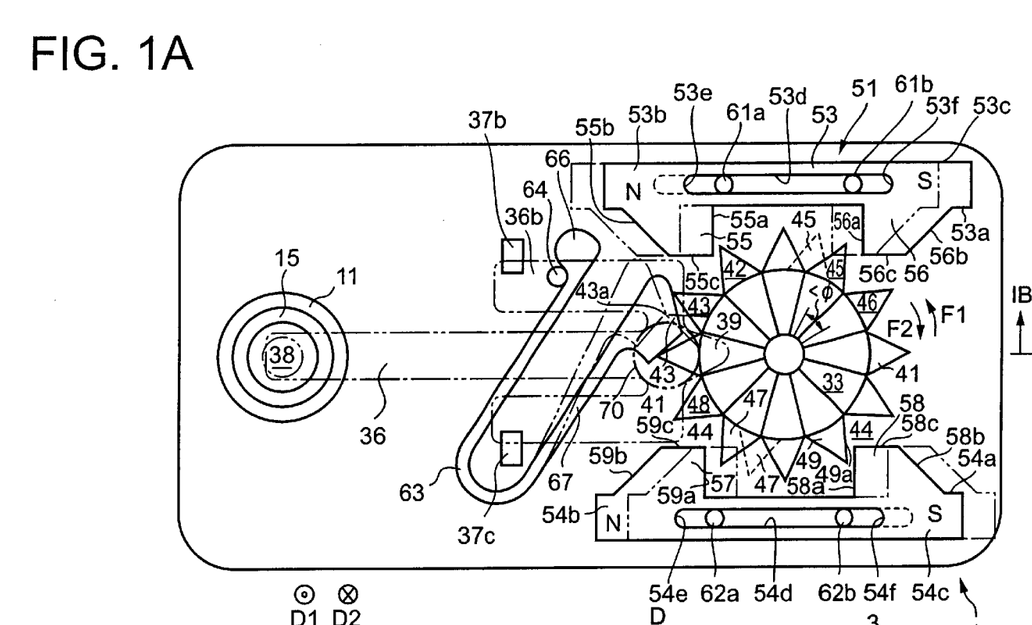
FIG. 1a is an explanatory plan view (in which the valve spring is indicated by an imaginary line)
Figure 1B:
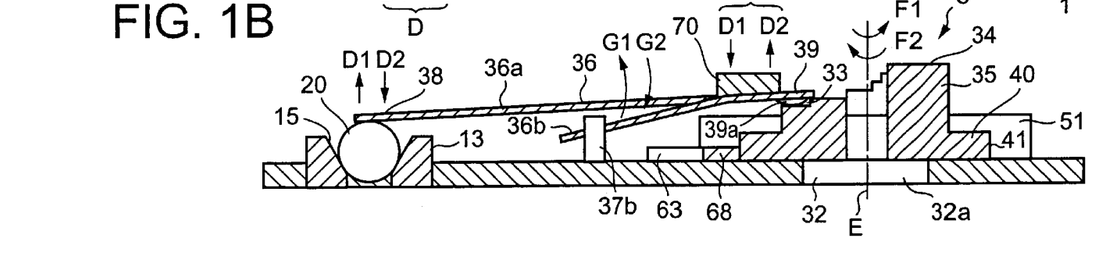
FIG. 1b is an explanatory sectional view taken along the line IB—IB of portion FIG. 1a, and FIG. 1c is a view of a set-pressure adjusting device for adjusting a set pressure of the pressure-variable valve device.
Figure 1C:
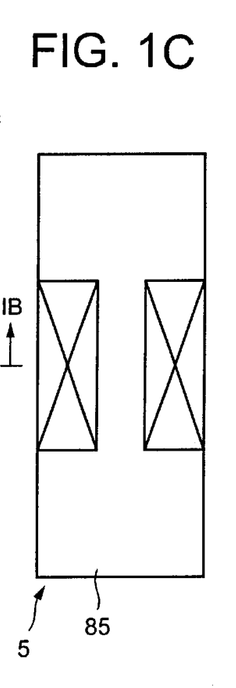
Figure 2:
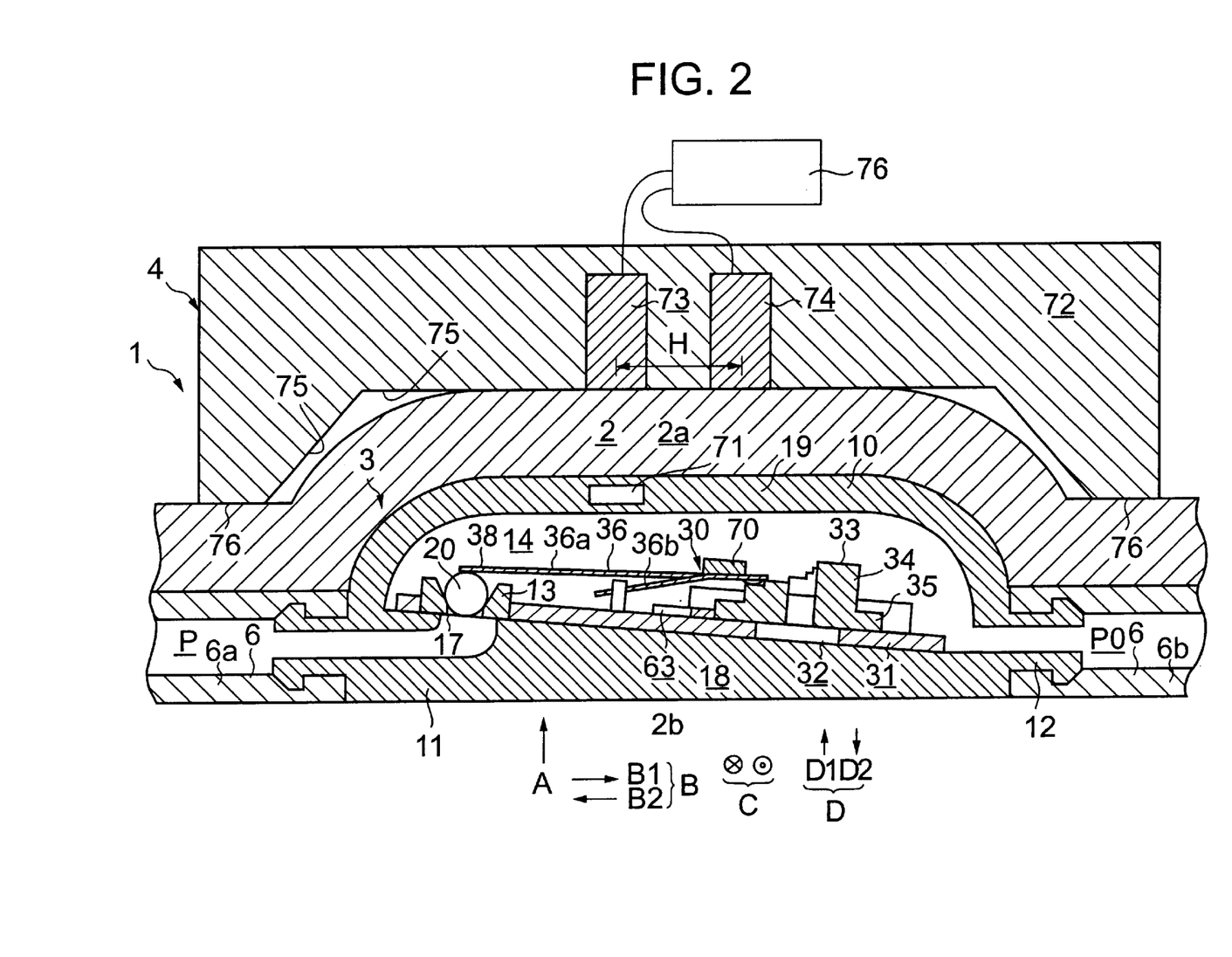
FIG. 2 is an explanatory sectional view similar to portion FIG. 1b, showing the pressure-variable valve device of FIGS. 1 in a state in which it is embedded in the human body, with a set-pressure detecting device being attached thereto.

FIGS. 1 through 4 show a valve system 1 according to a preferred embodiment of the present invention. As shown in FIG. 2, a valve system 1 has a pressure-variable valve device 3 embedded on a cranial bone 2b under, for example, a human scalp 2 (at the depth, for example, of several mm as measured from the body surface), a set-pressure detecting device 4 for detecting the set pressure $\Delta P$ set by the valve device 3, and a set-pressure adjusting device 5 for adjusting the set pressure $\Delta P$.

The valve device 3 is connected and arranged at some midpoint A of a duct 6 for spinal fluid, and setting/adjustment is effected such that the spinal fluid pressure P in the upstream-side duct or conduit 6a is not higher than the spinal fluid pressure P0 in a downstream-side duct or conduit 6b by more than the set pressure $\Delta P$ of the valve device 3, that is, that the spinal fluid pressure is not more than P0+$\Delta P$. For example, when the pressure P0 actually coincides with the atmospheric pressure, assuming that P0=0, with the atmospheric pressure serving as a reference, P=$\Delta P$. The valve device 3 may be used as a valve device for adjusting pressure such that the pressure of the downstream-side conduit 6b is not less than P0 (=P−$\Delta P$).

The valve device 3 has a valve-device main body or valve housing 10 which contains inlet- and outlet-side conduits 11 and 12, a chamber 14 communicating with the outlet-side conduit 12, and an opening 17 serving as a valve flow passage for connecting the inlet- and outlet-side conduits 11 and 12 and the chamber 14 and which is formed of silicon resin, polycarbonate or the like, a ball-like valve member or ball valve 20 which serves as a valve for opening and closing the opening 17 in the valve-device main body 10 and which is formed of a hard ceramic such as sapphire or ruby, and a pressure control mechanism 30 which, when the pressure P of the upstream-side conduit 6a exceeds the set pressure P0+$\Delta P$, cooperates with the ball valve 20 to cancel the closure of the flow passage 17 by the ball valve 20. The valve housing 10 has, for example, a length in the direction B of approximately 1 to 2 cms, a width in the direction C of approximately several mm to 1 cm, and a height in the direction D of approximately several mms to 1 cm. In some case, however, the sizes in the above directions may be smaller or larger accordingly than the ones mentioned above.

The valve-device main body 10 has a valve seat portion 13 on which the ball valve 20 can be seated between the inlet-side conduit 11 connected to the upstream-side conduit 6a and the outlet-side conduit 12 connected to the downstream-side conduit 6b and which is formed of the same material as the ball valve 20, and the chamber 14 accommodating the ball valve 20 and the pressure control mechanism 30. The valve seat portion 13 consists of a valve seat member provided with a truncated-cone-like seat surface 15. Although in the drawing the valve-device main body 10 is shown as if it consists of a single, member in order to make it easily understandable, the valve-device main body 10 is formed by assembling a plurality of portions such that various members can be arranged in the chamber 14.

As mainly shown in FIG. 1A and FIG. 1B, the pressure control mechanism 30 includes a substrate 31 fastened to the bottom wall 18 of the chamber 14, a cam axle or rotation center shaft 32 whose large-diameter portion 32a is fitted into the substrate 31, a cam wheel 35 serving as a rotating member which is fitted onto the small-diameter shaft portion 32b of the cam wheel 32 extending in the direction C perpendicular to the substrate 31 so as to be rotatable in directions F1 and F2 around the central axis E of the axle 32 and which is provided with a spiral multistage cam surface 33, and a valve spring 36 arranged between the cam 34 and the ball-like valve 20. The valve spring 36 is, for example, in a forked configuration provided with three leg portions or arm portions 36a, 36b and 36c. The forward ends of the shorter arm portions 36b and 36c on both sides are locked by engagement support structures 37b and 37c, and the forward end 38 of the longer, central arm portion 36a abuts against the ball 20, the forward end of a semi-spherical engagement protrusion 39a formed on the lower surface of the fork base end portion 39 positioned at the base end of the arm portion 36a being in contact with the cam surface 33 of the spiral cam 34. The valve seat member 13 is also fitted into a hole in the substrate 31. Numeral 70 indicates a permanent magnet serving as a set-pressure signal generating means or movable marker which is fastened onto the base end portion 39 of the valve spring 36 and which provides a magnetic field signal indicating the position of the base end portion 39 with respect to the direction D, and numeral 71 (FIG. 2) indicates a permanent magnet serving as a stationary marker which is embedded in the top wall 19 of the valve-device main body 10 and which provides a reference position signal indicating the position of the valve-device main body 10.

The valve spring 36 is formed of a non-magnetic metal material such as a non-magnetic stainless steel, and the width of each of the arm portions 36a, 36b and 36c and the interval therebetween is approximately 1 mm, the thickness of the arm portions being approximately 0.1 mm. The length of the arm portion 36a is approximately 1 to 2 cm, and the length of the arm portions 36b and 36c is approximately half the length of the arm portion 36a. In some cases, the sizes in the various directions may be smaller or larger accordingly than the ones mentioned above. While in this specification the terms: horizontal direction and vertical directions, are used based on the apparent directions in FIGS. 1 through 3, it will be obvious that these directions vary depending on the orientation of the human body in which the valve device 3 is embedded and the position in the body at which it is embedded.

Thus, when the cam wheel 35 is rotated around the small-diameter axle portion 32b of the cam axle 32 in the direction F1 or F2, the base end portion 39 of the valve spring 36 is moved in the direction D1 or D2 by the cam 34, and the condition of deflection in the direction G1 or G2 of the spring 36, the forward ends of the arm portions 36b and 36c of which are supported or locked by the engagement support structures 37b and 37c, varies to thereby vary the force with which the ball 20 is pressurized in the direction D2 by the forward end portion 38 of the spring 36, thereby varying the pressure at which the closure of the valve flow passage 17 by the ball 20 is canceled. The protrusion 39a of the arm base end portion 39 is engaged one of the spiral cam surfaces 33 to be stabilized, so that the cam wheel 35 takes a rotating position after intermittent rotation by a predetermined angle or pitch $\Delta\phi$. The position in the vertical direction D of the magnet 70 on the arm base end portion is in one-to-one correspondence with the position in the direction D of the protrusion 39a, that is, the pressurizing force applied in the direction D to the ball 20 by the valve spring 36, or in other words the set pressure $\Delta P$ of the valve.

A ratchet 40 is integrally formed underneath the large-diameter base portion 35a of the cam wheel 35 formed of a resin such as polycarbonate, and the ratchet 40, which has a large number of claws 41 in its outer periphery, is capable of rotating with the cam wheel 35 around the small-diameter axle portion 32b of the cam axle 32, that is, around the central axis E. It is also possible to prepare the ratchet 40 as a separate component formed of a metal such as non-magnetic stainless steel and fasten it to the cam wheel 35, formed of a similar material, such that they do not rotate relative to each other.

On either side of the ratchet 40 in the direction C, there are provided sliders 51 and 52, which are mounted to the substrate 31 so as to be slidable thereon in the directions B1 and B2. The sliders 51 and 52 include main body portions 53 and 54 which are long and narrow in the direction B and pairs of engagement pawls 55, 56 and 57, 58 integrally formed on side walls 53a and 54a facing the claws 41 of the ratchet 40. The slider main body portions 53 and 54 serving as the permanent magnet structures consist of permanent magnets which are magnetized in the same direction B2 and which are practically of the same construction and the same strength. The end portions 53b, 54b in the direction B1 of the main body portions 53 and 54 constitute N-poles, and the end portions 53c, 54c in the direction B2 thereof constitute S-poles. The slider main body portions 53 and 54 respectively have guide holes or elongated holes 53d and 54d extending in the direction B, and pairs of guide pins 61a, 61b and 62a, 62b, spaced apart from each other in the direction B and protruding from the substrate 31, are fitted into the elongated holes 53d and 54d. The diameter in the direction C of the guide pins 61a and 61b practically coincides with the width in the direction C of the elongated hole 53d, and the diameter in the direction C of the guide pins 62a and 62b practically coincides with the width in the direction C of the elongated hole 54d. Thus, the sliders 51 and 52, or the slider main body portions 53 and 54, are slidable relative to the substrate 31 in the direction B1 up to the positions where the end walls 53e and 54e abut against the peripheral surfaces of the guide pins 61a and 62a, and are slidable relative to the substrate 31 in the direction B2 up to the positions where the end walls 53f and 54f abut against the peripheral surfaces of the guide pins 61a and 62a.

The engagement pawl 55 has an inner engagement surface 55a which, when the slider 51 moves relative to the substrate 31 in the direction B1, abuts against and engages with an opposing surface 42a of the claw 42 of the claws 41 of the ratchet 40 that is nearest thereto in the direction B1, and pushes the claw 42 in the direction B1 to cause the ratchet 40 to rotate in the direction F2, an outer surface 55b determining the tapered configuration of the claw so as to be capable of being fitted with play into the gap between two adjacent claws 41 of the ratchet 40, for example, the gap 44 between claws 42 and 43, and an engagement surface 55c at the forward end. Similarly, the engagement pawl 56 has an inner engagement surface 56a which, when the slider 51 moves relative to the substrate 31 in the direction B2, abuts against and engages with an opposing surface 45a of the claw 45 of the claws 41 of the ratchet 40 that is nearest thereto in the direction B2, and pushes the claw 45 in the direction B2 to cause the ratchet 40 to rotate in the direction F1, an outer surface 56b determining the tapered configuration of the claw so as to be capable of being fitted with play into the gap between two adjacent claws 41 of the ratchet 40, for example, the gap 44 between claws 45 and 46, and an engagement surface 57c at the forward end.

Further, the engagement pawl 57 has an inner engagement surface 57a which, when the slider 52 moves relative to the substrate 31 in the direction B1, abuts against and engages with an opposing surface 47a of the claw 47 of the claws 41 of the ratchet 40 that is nearest thereto in the direction B1, and pushes the claw 47 in the direction B1 to cause the ratchet 40 to rotate in the direction F1, and an outer surface 57b determining the tapered configuration of the claw so as to be capable of being fitted with play into the gap between two adjacent claws of the ratchet 40, for example, the gap 44 between claws 47 and 48. Similarly, the engagement pawl 58 has an inner engagement surface 58a which, when the slider 52 moves relative to the substrate 31 in the direction B2, abuts against and engages with an opposing surface 49a of the claw 49 of the claws 41 of the ratchet 40 that is nearest thereto in the direction B2, and pushes the claw 49 in the direction B2 to cause the ratchet 40 to rotate in the direction F2, an outer surface 58b determining the tapered configuration of the claw so as to be capable of being fitted with play into the gap 44 between claws 49 and the claw adjacent thereto of the ratchet 40, and an engagement surface 58c at the forward end.

Free rotation of the ratchet 40 is restrained by a restraining spring or jumper spring 63. More specifically, an engagement portion 66 at the forward end of one arm portion 65 of the substantially U-shaped rotation restraining spring 63 is engaged with an engagement protrusion 64 protruding from the substrate 31. Due to the resilient force of the spring 63, an engagement portion 68 at the forward end of the other arm portion 67 of the spring is lightly pressed against the portion between adjacent claws 41 of the ratchet 40, whereby rotation in the direction F1, F2 of the ratchet 40 resulting from a movement of the embedded portion of the valve device 3 (e.g., the human head) or a light impact applied to the embedded portion is restrained and inhibited, locking the ratchet 40 at that position. Thus, there is little danger of unexpected rotation of the cam wheel 35 as the rotating member being caused to thereby cause unexpected fluctuations in the set pressure of the valve device 3. The rotation restraining force of the spring 63 is relatively small. Its magnitude is such that rotation of the ratchet 40 is permitted when the torques due to the sliders 51 and 52 are applied to the ratchet 40 at the same time and in the same rotating direction.

In this example, the displacement transmission mechanism is composed of the engagement pawls 55, 56, 57, 58 integrally formed with the sliders 53 and 54, the ratchet 40 integrally formed with the cam wheel 35, and the restraining spring 63, and the rotation control mechanism includes, in addition to the displacement transmission mechanism, the slider main bodies 53 and 54 serving as the permanent magnet structures. That is, the rotation control mechanism is composed of the sliders 51 and 52, the ratchet 40, and the restraining spring 63.

As shown in FIG. 2, the set-pressure detecting device 4 includes a detecting-device main body 72 placed on the protruding portion 2a at the position of the scalp 2a where the pressure-variable valve device 3 is embedded, and magnetic sensors 73 and 74 mounted in the main body 72. To accommodate the protruding portion 2a at the embedded portion of the scalp, the detecting-device main body 72 has a recess 75 of a configuration substantially complementary to the protruding portion 2a on its lower surface 76 coming into contact with the scalp 2. The magnetic sensor 73 is provided in the vicinity of the surface of the recess 75 so as to detect the magnetic field due to the permanent magnet 71 embedded in the top wall 19 of the main body 10 of the pressure-variable valve device 3. Similarly, the magnetic sensor 74 is provided in the vicinity of the surface of the recess 75 so as to detect the magnetic field due to the permanent magnet 70 secured to the base end portion 39 of the spring 36 of the pressure-variable valve device 3. The distance H between the magnetic sensors 73 and 74 is substantially equal to the distance between the magnets 71 and 70 in the direction B. The magnetic sensors 73 and 74 consist, for example, of giant magneto-resistance (GMR) effect elements. However, they may also consist of magneto-resistance (MR) effect elements or some other magnetic field sensors. The detection results obtained by the magnetic sensors 73 and 74 are displayed by a display device, such as a display 76.

When detecting the set pressure, positioning is first roughly effected by placing the detecting-device main body 72 such that the protruding portion 2a is fitted into the recess 75 of the detecting-device main body 72. Then, fine adjustment of the position and orientation of the detecting-device main body 72 in the directions B and C is performed while watching the two detection outputs on the display 76 such that the magnetic field detection output of the permanent magnet 71 obtained by the magnetic sensor 73 becomes maximum and that the magnetic field detection output of the permanent magnet 71 obtained by the magnetic sensor 74 becomes maximum. Next, from the detection result obtained by the magnetic sensor 74, that is, the magnitude of the detected magnetic field, information on the position in the direction D of the magnet 70 is obtained. If desired, it is also possible to correct the detection output obtained by the magnetic sensor 74, using the magnitude of the detection output of the magnet 71 obtained by the magnetic sensor 73 as a reference.

In the pressure-variable valve device 3, constructed as described above, the valve-device main body 10 and the substrate 31 (which may be integrally formed as a part of the valve-device main body 10) are formed of an MRI-free plastic material, the rotating member 35, the ratchet 40, the guide pins 61a, 61b, 62a, and 62b, the engagement support structures 37b and 37c, the restraining spring, and the valve spring 36 are formed of a plastic material or a non-magnetic metal material which is MRI-free, and the ball valve 20 and the valve seat member 13 are formed of an MRI-free ceramic material.

Figure 3:
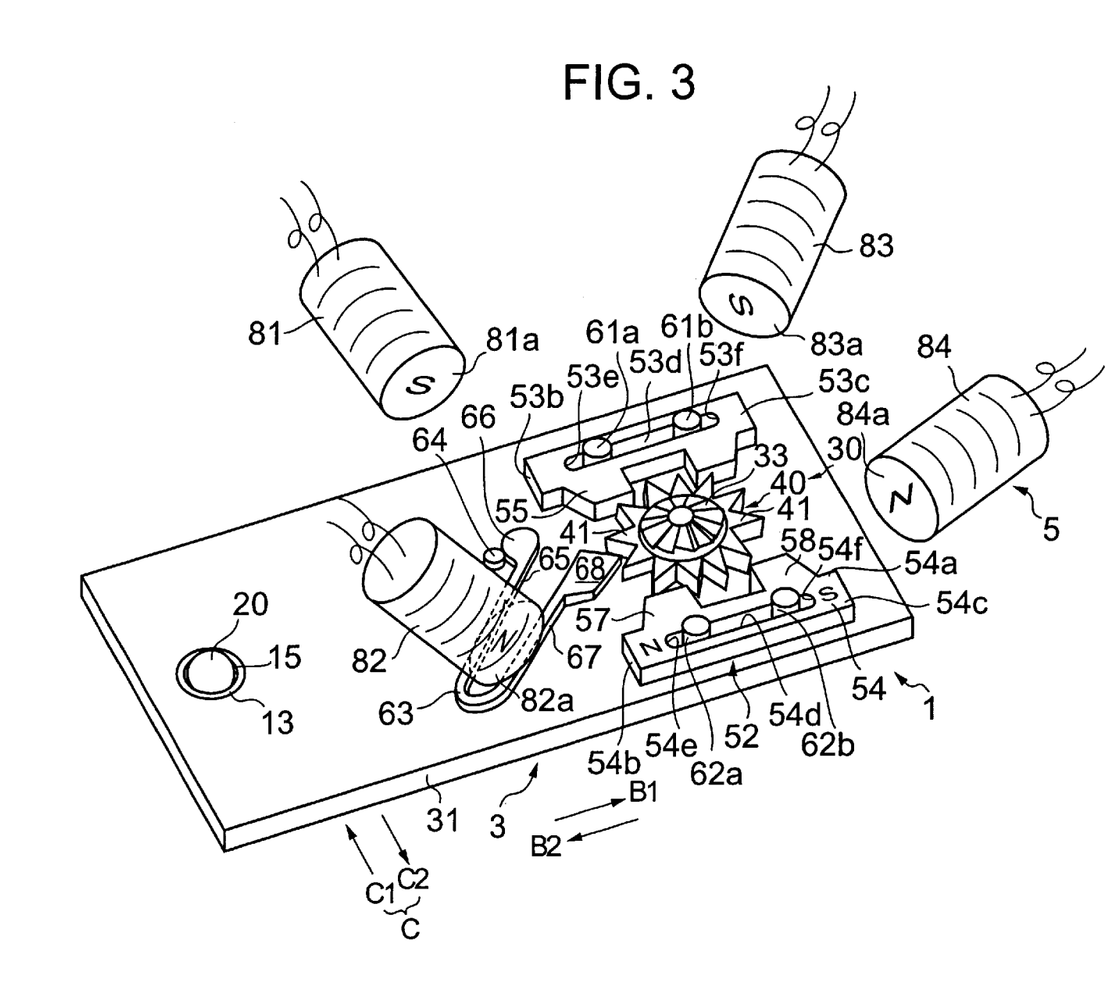
FIG. 3 is an explanatory perspective view showing how set-pressure adjustment for the pressure-variable valve device of FIG. 1 is performed by a set-pressure adjusting device (to make the drawing easier to understand, the valve-device main body is omitted)

As shown in FIGS. 1 and 3, and as shown in detail in FIG. 3, the set-pressure adjusting device 5 includes, for example, four electromagnets 81, 82, 83, and 84. The electromagnets 81, 82, 83, and 84 typically consist of solenoid coils and bar-shaped members inserted into the coils and formed of a high-permeability soft magnetic material. The four electromagnets 81, 82, 83, and 84 are obliquely mounted in the set-pressure adjusting device main body (not shown), having a configuration similar to that of the main body 72 of the set-pressure detecting device 4 shown in FIG. 2, such the lower end portions 81*a*, 83*a* and 82*a*, 84*a* of the electromagnets 81, 83 and 82, 84 are directed toward the end portions 53*b* and 53*c* of the slider main body 53 and the end portions 54*b* and 54*c* of the slider main body 54 and in close vicinity thereto. The electromagnets 81 and 82 may be formed by a single electromagnet (not shown). Further, as shown in FIG. 1, the electromagnets 83 and 84 may also be formed by a single electromagnet, for example, an electromagnet 85.

Next, mainly with reference to FIG. 4A through FIG. 4D, the process or operation for changing and setting the pressure of the pressure-variable valve device 3 using the set-pressure adjusting device 5 will be described in detail. FIG. 4A through FIG. 4D only show the energization condition of the lower end of an electromagnet in an energized state.

Figure 4A:
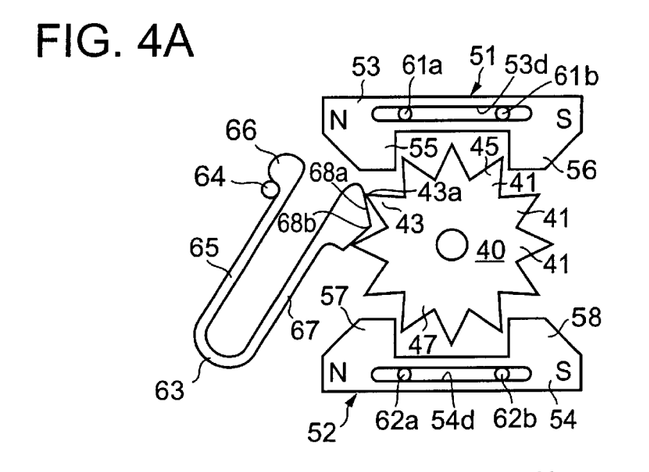
FIG. 4 are explanatory diagrams illustrating stepwise the operation of setting pressure in a valve, system using the pressure-variable valve device of FIG. 1.

First, suppose the initial state is as shown in FIG. 4A. In this state, the sliders 51 and 52 are at the position in which the guide pins 61*a*, 61*b*, 62*a*, and 62*b* are fitted with play in the guide holes or elongated holes 53*d* and 54*d* at the midpoints, and the engagement portion 68 at the forward end of the restraining spring 63 is engaged deeply with the portion between adjacent claws 41 of the ratchet 40 and lightly held in press contact therewith, the ratchet 40 and the cam wheel 35 being locked so as not to rotate, and rotation of the ratchet 40 and the cam wheel 35 being restrained by the restraining spring 63. None of the electromagnets 81, 82, 83, and 84 is energized. On the other hand, the sliders 51 and 52 can move freely in the directions B1 and B2 within a small range. The valve device 3 is set to a pressure corresponding to the rotating position of the ratchet 40.

For example, when, in the condition shown in FIG. 4A, a gigantic static magnetic field W like the main magnetic field in the Z-direction of an MRI apparatus is applied, for example, in the direction B2, the N-pole end portion 53*b* and the S-pole end portion 53*c* of the slider 51 respectively receives forces in opposite directions and of the same strength in the directions B2 and B1, so that the forced received by the slider 51 are balanced by each other, and the slider 51 is not moved, similarly in the case of the slider 52. This also applies to the case in which the magnetic poles of the slider main bodies 53 and 54 of the sliders 51 and 52 are distributed in places other than the end portions 53*b*, 53*b*, 54*b*, and 54*c*. Further, even when the direction of the static magnetic field W is a direction crossing the direction B, movements other than those in the directions B1 and B2 are inhibited by the guide pins 61*a* and 61*b*, and the influence of the components of the static magnetic field W in the directions B1 and B2 is the same, so that the sliders 51 and 52 are not moved by the static magnetic field W.

Further, even in the case in which the inclined magnetic field of an MRI apparatus is applied, no rotation of the ratchet 40 and the rotating member 35 is practically caused. Assuming that the force in the direction B2 applied to the N-pole end portion 53*b* of the slider 51 by the inclined magnetic field is larger than the force in the direction B1 applied to the S-pole end portion 53*c* by the inclined magnetic field, the engagement pawl 56 of the slider 51 will cause the ratchet 40 to rotate in the direction F1. Since the inclined magnetic field is applied to the main bodies (magnet structures) 53 and 54 of the sliders 51 and 52 substantially in the same manner, the force in the direction B2 applied to the N-pole end portion 54*b* of the slider 52 is larger than the force in the direction B1 applied to the S-pole end portion 54*c*, and the engagement pawl 58 of the slider 52 will cause the ratchet 40 to rotate in the direction F1. As a result, the torque in the direction F1 applied to the ratchet 40 by the slider 51 and the torque in the direction F2 applied to the ratchet 40 by the slider 52 are balanced by each other, so that the ratchet 40 and the rotating member 35 do not actually rotate. Even in the case in which there is a difference between the torque in the direction F1 and the torque in the direction F2, the inclined magnetic field is relatively small and the inclination of the inclined magnetic field is also relatively small, so that the torques of the sliders 51 and 52 are relatively small, and the difference in torque is still smaller. Thus, due to the rotation restraining force provided by the restraining spring 63 whose engagement end portion 68 is engaged between claws 41 of the ratchet 40, it is possible to reliably inhibit rotation of the ratchet 40.

Figure 4B:
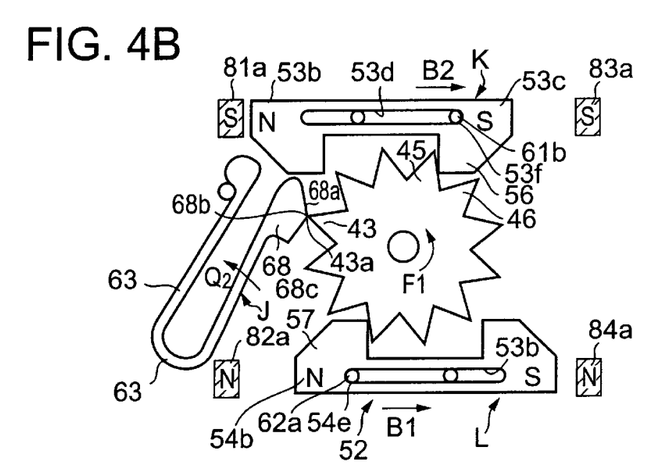

For example, as shown in FIG. 4B, when electricity is supplied to the coils of the electromagnets 81 and 83 to energize the electromagnets 81 and 83 such that the lower end 81*a* of the electromagnet 81 and the lower end 83*a* of the electromagnet 83 both constitute S-poles, the N-pole end portion 53*b* of the slider main body 53 of the slider 51 receives an attraction force from the S-pole end portion 81*a* of the adjacent electromagnet 81, and the S-pole end portion 53*c* of the slider main body 53 receives a repulsive force from the S-pole end portion 83*a* of the electromagnet 83, so that the slider main body 53 receives forces in the direction B2 from both the electromagnets 81 and 83, and the engagement pawl 56 pushes the adjacent claw 45 of the ratchet 40 in the direction B2 so as to cause the ratchet 40 to rotate in the direction F1.

Similarly, when electricity is supplied to the coils of the electromagnets 82 and 84 to energize the electromagnets 82 and 84 such that the lower end 82*a* of the electromagnet 82 and the lower end 84*a* of the electromagnet 84 both constitute N-poles, the N-pole end portion 54*b* of the slider main body 54 of the slider 52 receives a repulsive force from the N-pole end portion 82*a* of the adjacent electromagnet 82, and the S-pole end portion 54*c* of the slider main body 54 receives an attraction force from the N-pole end portion 84*a* of the electromagnet 84, so that the slider main body 54 receives forces in the direction B1 from both the electromagnets 82 and 84, and the engagement pawl 57 pushes the adjacent claw 47 of the ratchet 40 in the direction B1 so as to cause the ratchet 40 to rotate in the direction F1.

That is, the ratchet 40 receives torques in the direction F1 from both the sliders 51 and 52, so that the ratchet 40 is rotated in the direction F1 against the restraining force applied by the engagement end portion 68 of the restraining spring 63 while deflecting the arm portion 67 of the spring 63 in the direction Q2 to a position J (the position shown in FIG. 4B or the imaginary-line position of FIG. 1). As shown in FIG. 4B, this rotation in the direction F1 by the sliders 51 and 52 ends when the end portion 53*f* of the elongated hole 53*d* of the slider main body 53 abuts against the guide pin 61*b* (the imaginary line K of FIG. 1A) and when the end portion 54*e* of the elongated hole 54*d* of the slider main body 54 abuts against the guide pin 62*a* (the imaginary line L of FIG. 1A). At this time, the claws 45 and 47 of the ratchet 40 reach substantially intermediate positions indicated by imaginary lines in FIG. 1, and, as indicated by an imaginary line in FIG. 1A, the engagement end portion 68 of the restraining spring 63 goes over the apex or top portion 43*a* of the claw 43 to which it has been adjacent on the upstream side. That is, as shown in FIG. 4B, the apex or top portion 43*a* of the claw 43 is brought from the condition in which it is engaged with the upstream-side engagement surface 68*a* of the engagement end portion 68 of the restraining spring 63 to the condition in which it goes over the apex 68*b* to engage the downstream-side engagement surface 68*c* situated on the downstream side with respect to the apex 68*b*.

Figure 4C:
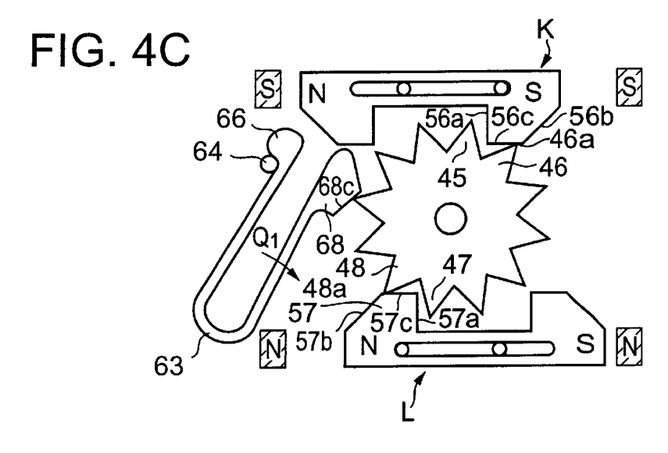

Thus, as shown in FIG. 4C, the ratchet 40 is further rotated in the direction F1 by the return force in the direction Q1 of the spring 63 which is applied to the top portion 43a of the claw 43 by the downstream-side engagement surface 68c of the restraining spring 63, and the apex 46a of the claw 46 of the ratchet 40 which comes after the claw 45 by one pitch abuts against the forward-end engagement surface 56c of the engagement pawl 56 of the slider 51 at the position K, the apex 48a of the claw 48 of the ratchet 40 which comes after the claw 47 by one pitch abutting against the forward-end engagement surface 57c of the engagement pawl 57 of the slider 52 at the position L to cause the rotation to stop.

Figure 4D:
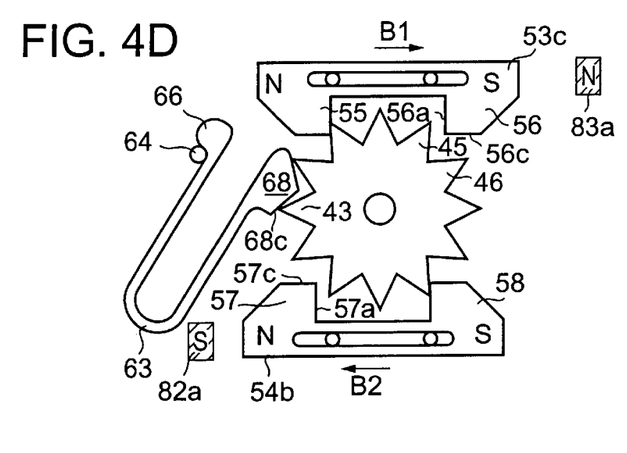

Next, the energization condition of the electromagnets 81, 82, 83, and 84 is changed. That is, for example, the supply of electricity to the coils of the electromagnets 81 and 84 is stopped, and the direction in which electricity is supplied to the coils of the electromagnets 82 and 83 is reversed to energize the electromagnets 82 and 83 such that the end portion 82a of the electromagnet 82 constitutes an S-pole and that the end portion 83a of the electromagnet 83 constitutes an N-pole. As a result, the end portion 53c of the slider 51 receives an attraction force in the direction B1 from the S-pole end portion 83a, and the end portion 54a of the slider 52 receives an attraction force in the direction B2 from the S-pole end portion 82a, the slider 51 being returned in the direction B1 and the slider 52 being returned in the direction B2 so that the forward-end engagement surfaces 56c and 57c of the engagement pawls 56 and 57 of the sliders 51 and 52 may move along the forward end portions 46a and 48a of the claws 47 and 48 of the ratchet 40. On the other hand, when, as a result of the movement of the sliders 51 and 52 in the directions B1 and B2, the engagement of the forward ends 46a and 48a of the claws 46 and 48 with the forward-end engagement surfaces 56c and 57c of the engagement claws 56 and 57 is canceled, the ratchet 40 is further rotated in the direction F1 by the engagement surface 68c of the end portion 68 of the restraining spring 63, and deeply engages the engagement end portion 68 of the spring 63, with the ratchet being rotated in the direction F1 by one pitch of the claw 41 as compared with the state shown in FIG. 4A (FIG. 4D). At this time, the sliders 51 and 52 are restored to the initial positions of FIG. 4A, in which the guide pins 62a, 62b and 62a and 62b are fitted with play in the elongated holes 53d and 54d at the intermediate positions. In this engaged state, the rotation restraining force due to the engagement of the engagement end portion 68 of the spring 63 with the claw 41 of the ratchet 40 is stronger than the rotation controlling force applied to one end portions 53c and 54b of the sliders 51 and 52, so that, even when the engagement pawls 55 and 58 abut against claws 41 of the ratchet 40, the ratchet 40 makes no further rotation. It is also possible to energize the electromagnets 81 and 84 instead of the electromagnets 82 and 83. Further, instead of energizing solely a part of the coils related to the movement of the sliders 51 and 52, it is also possible to energize all the relevant coils, for example, for a short period of time or at a low energization level, or for a short period of time and at a low energization level. Further, it is also possible to provide only the electromagnets 81 and 82 or only the electromagnets 83 and 84, energizing them in at least two stages of energization level.

To rotate the ratchet 40 by only one pitch, the supply of electricity to the coils is stopped, and, to rotate it by still another pitch, the steps of FIG. 4A through FIG. 4D are repeated. To further rotate the ratchet 40 in the direction F1, the above-described steps or operations are repeated. To rotate the ratchet 40 in reverse direction, the direction in which electricity is supplied to the electromagnets 81, 82, 83, and 84 is reversed from that in the above-described case.

Each time the ratchet 40 is rotated by one pitch in the direction, F1 or F2, the cam wheel 35 is rotated by one pitch in the direction F1 or F2 to cause the spiral cam surface 33 with which the protrusion 39a of the base end portion 39 of the spring 36 is engaged to vary by one pitch, and to cause the position in the direction D of the base end portion 39 of the spring 36, so that the force with which the valve 20 is pressurized in the direction D by the spring 36 varies by an amount corresponding to one pitch, and the set pressure ΔP of the pressure-variable valve device 3 is also increased or decreased to a degree corresponding to one pitch.

Thus, after detecting and confirming the set pressure ΔP of the pressure-variable valve device 3 by the set-pressure detecting device 4, the set pressure ΔP of the pressure-variable valve device 3 is varied and adjusted by the set-pressure adjusting device 5. Typically, the adjustment of the set pressure ΔP is effected after the detection thereof, so that it is possible to integrally incorporate the electromagnets 81, 82, 83, and 84 into the main body 72 of the set-pressure detecting device 4. In the case in which the set pressure is known beforehand, it is possible to solely vary and adjust the set pressure ΔP.

Figure 5:
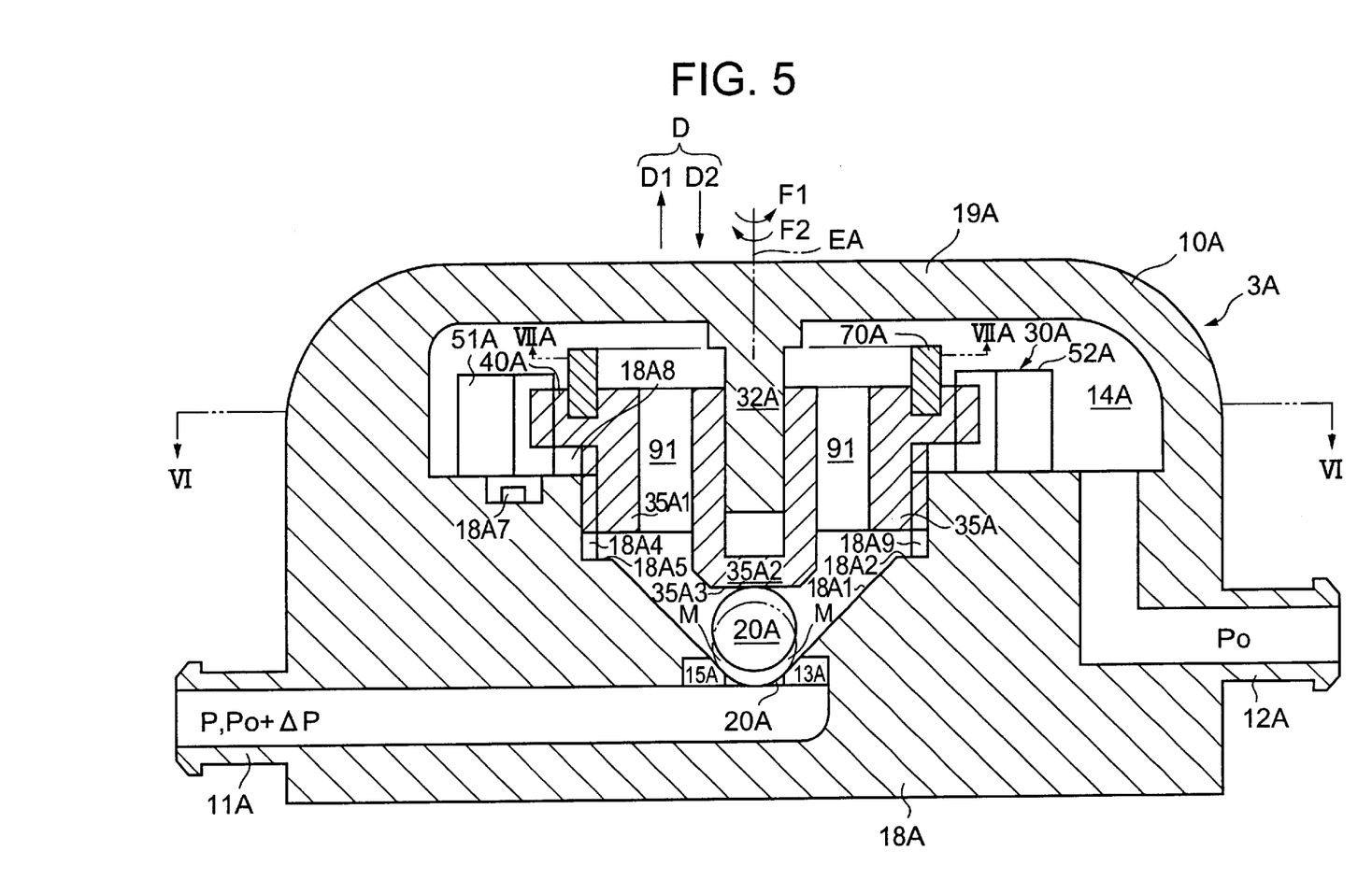
FIG. 5 is an explanatory sectional view taken along the line V—V of FIG. 6, showing a pressure-variable valve device according to another preferred embodiment of the present invention from a direction similar to that of FIG. 2.
Figure 6:
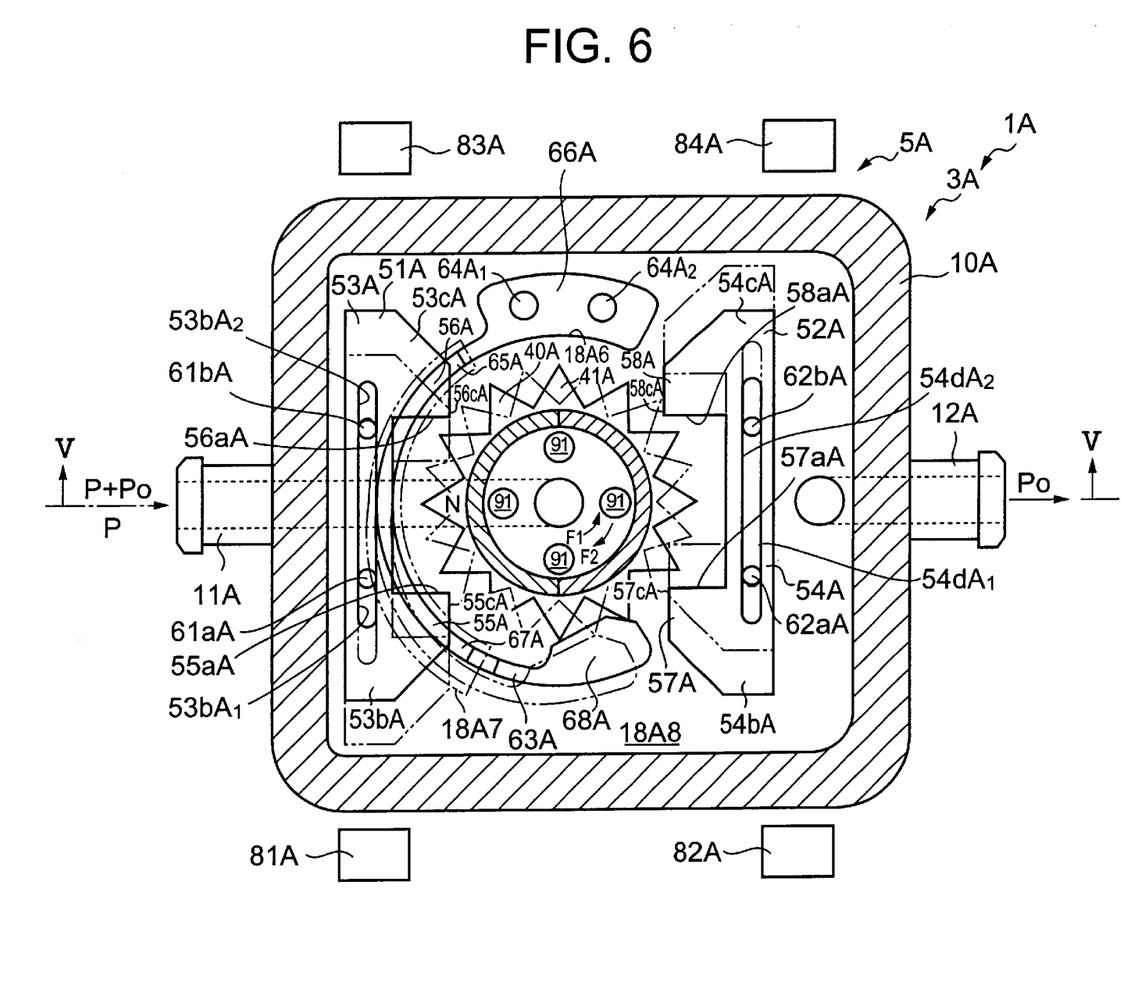
FIG. 6 is an explanatory sectional view taken along the line VI—VI of FIG. 5.
Figure 7A:
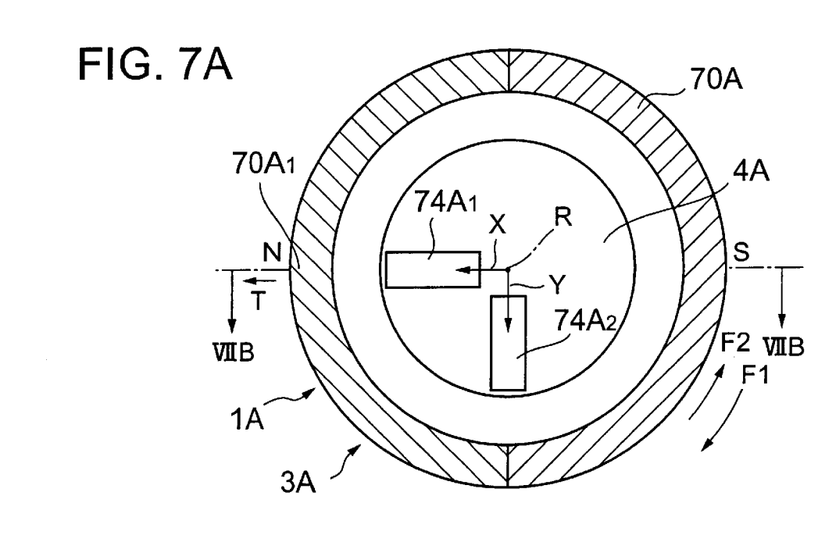
FIG. 7a is an explanatory sectional view taken along the line VIIA—VIIA of FIG. 4 (The valve-device main body and the portion in which the valve device is embedded, such as the scalp, are omitted)
Figure 7B:
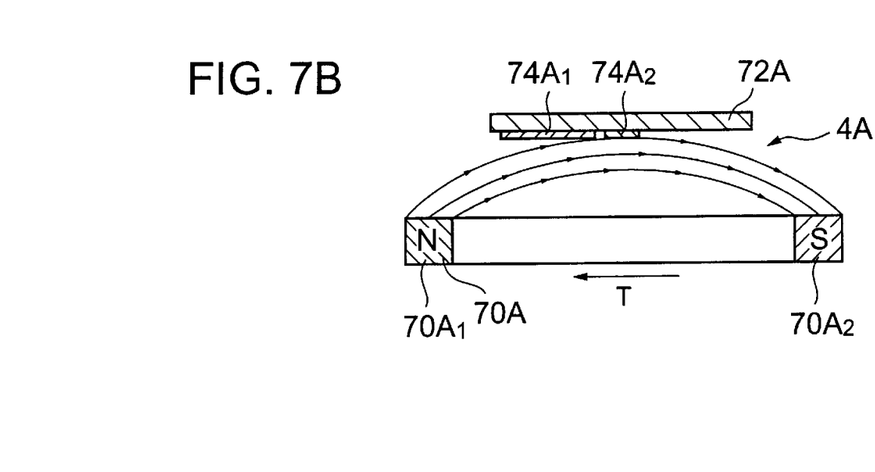
FIG. 7b is an explanatory sectional view taken along the line VIIB—VIIB of FIG. 7a, and FIG. 7c is a graph schematically showing sensor detection output.

FIGS. 5 through 7 show a pressure-variable valve device according to another preferred embodiment of the present invention and a valve system using the valve device. In the embodiment shown in FIGS. 5 through 7, the devices, members, positions and elements which are substantially the same with or similar to those of the embodiment shown in FIGS. 1 through 4 in terms of function are indicated by the same reference numerals, with symbol A being added to the numerals. Thus, the components having the same reference numerals as those of the embodiment shown in FIGS. 1 through 4 except for the fact that the numerals have symbol A function substantially in the same manner as those of the embodiment shown in FIGS. 1 through 4 unless particularly described in this specification or except for the cases in which a difference is obvious from the description of the device or system shown in FIGS. 5 through 7. Regarding the directions of movement and the conditions indicated by symbols in the form of capital letters are kept the same insofar as correspondence is allowed.

In the pressure-variable valve device 3A shown in FIGS. 5 through 7, a valve housing or valve-device main body 10A contains in a chamber 14A between inlet- and outlet-side ducts 11A and 12A and a pressure control mechanism 30A for controlling the size M of an aperture 17A between a valve seat member 13A and a ball valve 20A. The differential pressure ΔP between the pressure P (which is equal to P0+ΔP) on the upstream side of the aperture flow passage 17A of the valve device 3A and the pressure P0 on the downstream side thereof depends on the size M of the aperture 17A and is uniquely determined as ΔP=ΔP (M). Thus, by varying the size M of the opening 17A, it is possible to set and control the pressure on the upstream side or on the downstream side (P0+ΔP) or (P−ΔP), using the pressure on the downstream side or upstream side P0 or P as a reference. The valve-device main body 10A is also formed by assembling a plurality of portions so that various members may be arranged inside the chamber 14.

In the bottom wall 18A of the valve-device main body 10A, there are provided a truncated-cone-shaped first flow passage formation hole 18A1 having a peripheral surface continuously connected to the seat surface 15A of the valve seat portion 13A, and a large-diameter second flow passage formation hole 18A3 extending from the upper end of the hole 18A1 through a step portion 18A2 to the chamber 14A, and a female screw portion 18A4 is provided in the peripheral wall of the second flow passage formation hole 18A3 so as to practically extend over the entire length thereof.

The pressure control mechanism 30A includes a central shaft portion 32A extending integrally and downwardly from the top wall 19A of the valve-device main body 10A, a movable member 35A which is rotatable around the central axis EA thereof relative to the shaft portion 32A, a ratchet 40A which is integral with the rotating member 35A, sliders 51A and 52A which can be engaged with the ratchet 40A, and a restraining spring 63A in the form of a lever.

The rotating member 35A has a male screw portion 35A1 threadedly engaged with the female screw portion 18A4 in the bottom wall 18A of the valve-device main body 10A, and the rotating member 35A and the ratchet 40A, which is integral therewith, are capable of moving in the directions D1 and D2 in accordance with rotation in the directions F1 and F2. In the rotating member 35A and the ratchet 40A, which is integral therewith, there are formed a plurality of (four, in the example shown in FIG. 6) axially extending communication holes or inner flow passages 91, which allow the flow passage 18A5 in the holes 18A1 and 18A3 to communicate with the chamber 14. Further, in the central portion of the rotating member 35A, there is formed a shaft portion 35A2 protruding in the direction of the axis EA toward the valve seat portion 13A. The lower end surface 35A3 of the shaft portion 35A2 supports the ball valve 20A brought into contact therewith by a flow of spinal fluid or the like caused by the differential pressure ΔP, and determines the amount by which the ball valve 20A is lifted in the direction of the axis EA, thereby determining the size M of the aperture 17A through cooperation with the truncated-cone-shaped hole 18A1. When the rotating member 35A is displaced in the direction D1, D2 in accordance with the angle of rotation in the directions F1, F2, the end surface 35A3 is also displaced accordingly in the direction D1, D2, whereby the amount by which the ball valve 20A is lifted in the direction D1 is increased or decreased, the size M of the aperture 17A is increased or decreased, and the set pressure of the valve device 3A is lowered or raised.

The ratchet 40A is integrally formed in the upper portion of the rotating member 35A (FIG. 5), and the claws 41A of the ratchet 40A can be engaged with engagement pawls 55A, 56A and 57A, 58A of sliders 51A and 52A capable of moving in the directions B1 and B2 along the bottom wall 18A of the chamber 14A (FIG. 6). In this example, the engagement pawls 55A, 56A, 57A, and 58A have engagement surfaces 55*a*A, 56*a*A, 57*a*A, and 58*a*A for rotating the relevant claw 41A of the ratchet 40A, and locking surfaces 55*c*A, 56*c*A, 57*c*A, and 58*c*A for the forward end 41*a*A of the claw 41A.

Further, in this example, the main body portion 53A of the slider 51A has two guide holes or elongated holes 53*d*A1 and 53*d*A2 into which guide pins 61*a*A and 61*b*A are inserted with play so that the slider can slide in the directions B1 and B2, and the slider main body portion 54A of the slider 51A has two guide holes or elongated holes 54*d*A1 and 54*d*A2 into which guide pins 62*a*A and 62*b*A are inserted with play so that the slider can slide in the directions B1 and B2. In this case also, the end portions 53*b*A and 53*c*A of the slider main body portion 53A serving as a magnet structure constitute magnetic poles of the same polarity as the adjacent end portions 54*b*A and 54*c*A of the slider main body portion 54A serving as a magnet structure.

The restraining lever 63A serving as the restraining spring has a base end portion 66A having a large thickness in the direction D, which is embedded and fixed in a recess 18A6 of a complementary configuration in the bottom wall 18A of the valve-device main body 10A by means of pins 64A1 and 64A2, and has a base-end-side elastic arm portion 65A which is fitted with play along a wide groove portion 18A7 arcuately extending from the recess 18A6 and which has a small thickness in the direction D and is of a small width. An arcuate elastic arm portion 67A at the forward end of the restraining lever 63A is raised obliquely such that the portion 67A1 spaced apart from the slide region of the slider 51A and when nearer the forward end 68A, is positioned in the direction D1, extends upwardly above the upper surface 18A8 of the bottom wall 18A of the chamber 14A, and then extending parallel to the upper surface 18A8 of the bottom wall 18A of the chamber 14A up to the engagement portion 68A at the forward end. The forward-end engagement portion 68A of the restraining lever 63A is engaged with a claw 41A of the ratchet 40A at a position where it is diametrally opposed to the base end portion 66A with respect to the central axis EA.

In this valve system 1A, the control of the rotating position of the rotating member 35A, which serves as an intermediary for the engagement of the engagement pawls 55A, 56A, 57A, and 58A of the sliders 51A and 52A with the claws 41A of the ratchet 40A, can be conducted in the same manner as in the case of the valve system 1 shown in FIGS. 4, etc. through selective energization control of the electromagnets 81A, 82A, 83A, and 84A constituting the set-pressure adjusting device 5A. Further, as in the case of the valve device 3 shown in FIGS. 1 through 4, in this valve device 3A, no rotation of the rotating member 35A is caused in an uneven magnetic field like the main magnetic field in the Z-direction of an MRI apparatus or in an inclined magnetic field. Further, as in the case of the valve device 3, in this valve device 3A, the restraining lever 63A inhibits or restrains free rotation of the ratchet 40A and the rotating member 35A which is integral therewith. Unlike the case of the valve device 3, in which the set pressure value is determined by the magnitude of the resilient force of the spring 36, in this valve device 3A, the set pressure value is determined by the position in the direction D of the rotating member 35A, whereby it is possible to reduce the production tolerance of the device. Further, it is possible to minimize the fear of secular changes such as a change in spring constant due to a deterioration of the spring.

In the upper surface of the ratchet 40A, there is formed an annular groove, in which the lower half of an annular permanent magnet 70A is fitted and secured. As shown, for example, in FIG. 7A and FIG. 7B, this annular permanent magnet 70A is diametrally magnetized, and one end 70A1 with respect to the diametral direction P constitutes an N-pole, the other end 70A2 constituting an S-pole.

Figure 7C:
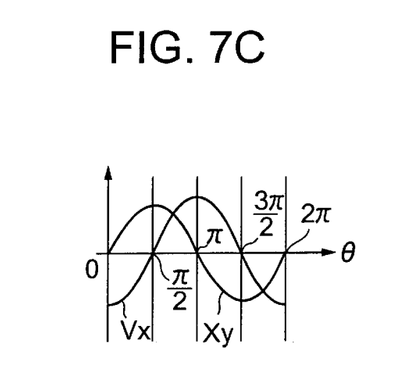

The set-pressure detecting device 4A has on the lower surface or in the lower portion of the main body 72A thereof a highly directional X-direction magnetic sensor 74A1 and Y-direction magnetic sensor 74A2 adapted to selectively detect solely magnetic fields of two orthogonal-axis directions: the X- and Y-axis directions. Thus, typically, from a relative rotating position at which the direction T coincides with the direction X, the magnetic-field detection output Vx obtained by the X-direction magnetic sensor 74A1 and the magnetic-field detection output Vy obtained by the Y-direction magnetic sensor 74A2 fluctuates as shown in FIG. 7C in accordance with the angle θ of rotation of the permanent magnet 70A in the direction F2 as a result of the rotation of the ratchet 40A and the rotating member 35A in the direction F2. Thus, by detecting Vx and Vy, it is possible to detect the set pressure ΔP at that time. Thus, on the basis of this detection value, the set pressure of the valve device 3A is adjusted by using the set-pressure adjusting device 5A. It is possible to adopt some other position detecting means to perform positioning such that the central position R of the X- and Y-direction magnetic sensors 74A1 and 74A2 coincides with the central axis EA of the rotating member 35A and that, for example, the Y-axis direction of the detecting-device main body 72A coincides with the direction B1.

What is claimed is:

1. A pressure-variable valve device comprising: a main body; a rotating member rotatably mounted within the main body to be rotatable about a central axis to vary a set pressure of the valve device; and a rotation control mechanism for controlling rotation of the rotating member and comprising at least one permanent magnet structure supported by the main body to undergo linear reciprocal movement and a displacement transmission mechanism for converting the linear movement of the at least one permanent magnet structure into angular movement of the rotating member in a direction corresponding to the direction of linear movement of the permanent magnet structure.

2. A pressure-variable valve device according to claim 1; further comprising set-pressure signal generating means for generating a set-pressure signal indicating a set pressure of the valve device and having a movable magnet which is mounted to undergo rotation around the rotation axis in accordance with an angular position of the rotating member.

3. A pressure-variable valve device according to claim 1; wherein the set pressure of the valve device is varied in accordance with the angular position of the rotating member.

4. A pressure-variable valve device according to claim 1; wherein the size of a fluid conduit releasably closed by the valve device is varied in accordance with a variation in angular position of the rotating member.

5. A pressure-variable valve device according to claim 1; wherein the main body is formed of a material which cannot be seen in an MRI image.

6. A pressure-variable valve device according to claim 1; wherein the main body is configured to be embedded in a human body to adjust a pressure of cerebrospinal fluid.

7. A pressure-variable valve device according to claim 1; wherein the main body defines a fluid conduit and has a fluid inlet port and a fluid discharge port, and the size of the fluid conduit releasably closed by the valve device is varied in accordance with a variation in angular position of the rotating member.

8. A pressure-variable valve device according to claim 1; further comprising a valve element disposed in the main body for releasably closing the fluid conduit.

9. A pressure-variable valve device according to claim 8; wherein the valve element has a ball-and-seat construction comprising a ball, a valve seat covered by the ball, a spring member having one end biasing the ball against the valve seat and a second end opposite the first end in contact with a spiral cam face of the rotating member.

10. A set-pressure adjusting device comprising: a housing; and magnetic field generating means disposed in the housing for applying a magnetic field to the at least one permanent magnet structure of the pressure-variable valve device according to claim 1 so as to cause the permanent magnet structure to undergo linear movement to angularly displace the rotating member to thereby adjust the set-pressure of the valve device.

11. A set-pressure adjusting device according to claim 10; wherein the magnetic field generating means comprises an electromagnet.

12. A pressure-variable valve device according to claim 1; wherein the at least one permanent magnet structure comprises a pair of permanent magnet structures proximate the rotating member, and the displacement transmission mechanism is configured such that when substantially the same external magnetic field is applied to both of the permanent magnet structures, mutually balancing, reverse magnitude torques are applied to the rotating member so that the external magnetic field does not cause angular movement of the rotating member.

13. A pressure-variable valve device according to claim 12; wherein the pair of permanent magnet structures are substantially opposed to each other in a diametral direction with respect to the central axis of the rotating member to undergo linear movement substantially in parallel along an axis crossing the diametral direction, and the permanent magnet structures have magnetic poles of the same polarity at ends thereof on the same side with respect to the direction of linear movement, and the displacement transmission mechanism comprises a projection provided on the respective permanent magnet structures that comes in contact with an adjacent portion of the rotating member to angularly displace the rotating member in one or the other direction upon linear movement of the respective permanent magnet structures in one or the other direction.

14. A pressure-variable valve device according to claim 12; further comprising set-pressure signal generating means for generating a set-pressure signal indicating a set pressure of the valve device and having a movable magnet which is displaced in a direction parallel to the central axis of the rotating member in accordance with an angular position of the rotating member.

15. A set-pressure adjusting device comprising: a housing; and magnetic field generating means disposed in the housing for applying a magnetic field to each of the pair of magnet structures of the pressure-variable valve device according to claim 2 to apply torques in the same direction to the rotating member to thereby adjust the set-pressure of the valve device.

16. A set-pressure adjusting device according to claim 15; wherein the magnetic field generating means comprises an electromagnet.

17. A pressure-variable valve device according to claim 12; wherein the pair of permanent magnet structures are mounted in the main body substantially opposed to each other in a diametral direction with respect to the central axis of the rotating member to undergo linear movement substantially in parallel along an axis crossing the diametral direction, and the permanent magnet structures have magnetic poles of the same polarity at ends thereof on the same side with respect to the direction of linear movement, and the displacement transmission mechanism comprises a projection provided on the respective permanent magnet structures that comes in contact with an adjacent portion of the rotating member to angularly displace the rotating member in a direction corresponding to the direction of linear movement of the respective permanent magnet structures.

18. A pressure-variable valve device according to claim 17; wherein each permanent magnet structure has an elongated slot engaged with guide pins provided in the main body to allow linear reciprocal movement of the permanent magnet structure along a given line.

19. A pressure-variable valve device according to claim 17; wherein the displacement transmission mechanism includes a ratchet coaxial with the rotating member to undergo rotational movement therewith and having a plurality of claws extending radially therefrom, and the projection comprises an engagement pawl provided on each permanent magnet structure for engaging a claw of the ratchet adjacent thereto when each permanent magnet structure undergoes linear movement.

20. A pressure-variable valve device according to claim 19; wherein the rotation control mechanism further comprises a restraining spring mounted in the main body and having one end engaged with the main body to cooperate with the engagement pawl of the permanent magnet structures to cause the rotating member to undergo intermittent rotation and an opposite end elastically biased against an adjacent claw of the ratchet to apply a weak restraining force thereto to restrain the rotating member from undesired angular movement while permitting angular movement of the rotating member by the pair of permanent magnet structures.

* * * * *